(12) United States Patent
Halpern

(10) Patent No.: US 6,770,021 B2
(45) Date of Patent: Aug. 3, 2004

(54) NEUTRON BRACHYTHERAPY DEVICE AND METHOD

(75) Inventor: David Halpern, Alpharetta, GA (US)

(73) Assignee: Isotron, Inc., Alpharetta, GA (US)

( * ) Notice: Subject to any disclaimer, the term of this patent is extended or adjusted under 35 U.S.C. 154(b) by 0 days.

(21) Appl. No.: 10/035,493

(22) Filed: Nov. 8, 2001

(65) Prior Publication Data

US 2002/0058851 A1 May 16, 2002

Related U.S. Application Data

(63) Continuation of application No. 09/395,324, filed on Sep. 13, 1999, now Pat. No. 6,352,500.

(51) Int. Cl.$^7$ .................................................. A61N 5/00
(52) U.S. Cl. ............................................... 600/8; 600/3
(58) Field of Search ......................................... 600/1–8

(56) References Cited

U.S. PATENT DOCUMENTS

| | | |
|---|---|---|
| 4,112,306 A | 9/1978 | Nunan |
| 4,150,298 A | 4/1979 | Brault et al. |
| 4,197,170 A | 4/1980 | Malson et al. |
| 4,508,119 A | 4/1985 | Tukamoto |
| 4,510,924 A | 4/1985 | Gray |
| 4,760,266 A | 7/1988 | Schulz |
| 4,763,642 A | 8/1988 | Horowitz |
| 4,819,618 A | 4/1989 | Liprie |
| 4,851,694 A | 7/1989 | Rague et al. |
| 4,853,550 A | 8/1989 | Schulz |
| H669 H | 9/1989 | Fairchild et al. |
| 4,891,165 A | 1/1990 | Suthanthrian |
| 4,897,076 A | 1/1990 | Puthawala et al. |
| 4,957,476 A | 9/1990 | Cano |
| 4,963,128 A | 10/1990 | Daniel et al. |
| 4,994,013 A | 2/1991 | Suthanthiran et al. |
| 5,084,002 A | 1/1992 | Liprie |
| 5,092,834 A | 3/1992 | Bradshaw et al. |
| 5,139,473 A | 8/1992 | Bradshaw et al. |
| 5,141,487 A | 8/1992 | Liprie |
| 5,183,455 A | 2/1993 | Hayman et al. |
| 5,199,939 A | 4/1993 | Dake et al. |
| 5,267,960 A | 12/1993 | Hayman et al. |
| 5,282,781 A | 2/1994 | Liprie |

(List continued on next page.)

OTHER PUBLICATIONS

Progress Report $^{252}$ Cf Radiation Oncology Study and Evaluation Project, Oct. 30, 1991.

S.S. Regachary, M.D., "Frontal Lobectomy", Neurosurgical Operative Atlas, vol. 3, American Association of Neurological Surgeons (1993) pp. 175–183.

J.D. McDonald, M.D. et al., "Interstitial Brachytherapy", Neurosurgical Operative Atlas, vol. 2, American Association of Neurosurgical Surgeons (1992) pp. 143–151.

P.J. Kelly, M.D., "Computer–Directed Sterotactic Resection of Brain Tumors", Neurosurgical Operative Atlas, vol. 2 American Association of Neurosurgical Surgeons (1991) pp. 299–313.

(List continued on next page.)

Primary Examiner—Samuel G. Gilbert
(74) Attorney, Agent, or Firm—Gray Cary Ware & Freidenrich LLP

(57) ABSTRACT

A neutron source for neutron brachytherapy is disclosed that may generate neutrons to treat cancer and other tumors. The neutron source in accordance with the invention may include a capsule into which the neutron emitting material is loaded and a guide wire. A coiled wire may be placed around the capsule and the guide wire to strengthen the capsule and guide wire. In accordance with one embodiment, the capsule containing the neutron emitting material is sufficiently thin so that the helium gas generated during the decay of the neutron emitting material may escape into the atmosphere. In a preferred embodiment, the neutron emitting material may be Californium ($Cf^{225}$).

40 Claims, 9 Drawing Sheets

U.S. PATENT DOCUMENTS

| | | |
|---|---|---|
| 5,317,616 A | 5/1994 | Swerdloff et al. |
| 5,322,499 A | 6/1994 | Liprie |
| 5,342,283 A | 8/1994 | Good |
| 5,364,336 A | 11/1994 | Carr |
| 5,395,300 A | 3/1995 | Liprie |
| 5,480,382 A | 1/1996 | Hammerslag et al. |
| 5,498,227 A | 3/1996 | Mawad |
| 5,503,614 A | 4/1996 | Liprie |
| 5,531,662 A | 7/1996 | Carr |
| 5,562,594 A | 10/1996 | Weeks |
| 5,575,749 A | 11/1996 | Liprie |
| 5,599,796 A | 2/1997 | Schinazi et al. |
| 5,616,114 A | 4/1997 | Thornton et al. |
| 5,618,266 A | 4/1997 | Liprie |
| 5,624,372 A | 4/1997 | Liprie |
| 5,643,171 A | 7/1997 | Bradshaw et al. |
| 5,662,580 A | 9/1997 | Bradshaw et al. |
| 5,713,828 A | 2/1998 | Coniglione |
| 5,720,717 A | 2/1998 | D'Andrea |
| 5,722,985 A | 3/1998 | Pettus |
| 5,782,741 A | 7/1998 | Bradshaw et al. |
| 5,788,713 A | 8/1998 | Dubach et al. |
| 5,800,333 A | 9/1998 | Liprie |
| 5,803,895 A | 9/1998 | Kronholz et al. |
| 5,807,231 A | 9/1998 | Liprie |
| 5,833,593 A | 11/1998 | Liprie |
| 5,840,008 A | 11/1998 | Klein et al. |
| 5,851,172 A | 12/1998 | Bueche et al. |
| 5,857,956 A | 1/1999 | Liprie |
| 5,860,909 A | 1/1999 | Mich et al. |
| 5,863,284 A | 1/1999 | Klein |
| 5,866,127 A | 2/1999 | Senger et al. |
| 5,868,757 A | 2/1999 | Koutrouvelis |
| 5,872,107 A | 2/1999 | Schinazi et al. |
| 5,882,291 A | 3/1999 | Bradshaw et al. |
| 6,019,736 A | 2/2000 | Avellanet et al. |
| 6,352,500 B1 * | 3/2002 | Halpern .................. 600/3 |

OTHER PUBLICATIONS

Raymond D. Adams, M.A., M.D., et al., "The Major Categories of Neurologic Disease", Principles of Neurology, Part IV, CH. 30, pp. 446–455, 1981.

R.C. Martin et al., "Development of High–Activity $^{252}$Cf Sources for Neutron Brachytherapy", Pergamon (1997) pp. 1657–1570.

R.A. Patchell, M.D. et al. "A Phase I Trial of Neutron Brachytherapy for the Treatment of Malignant Gliomas" The British Journal of Radiology, (1997) pp. 1162–1167.

Rolf. F. Barth, et al., "Borton Neutron Capture Therapy for Cancer", Scientific American, Oct. 1990, pp. 100–107.

Yosh Maruyama, M.D., FACR, et al., "Study of Biological Effects of Varying Mixtures of Cf–252 and Gamma Radiation on the Acute Radiation Syndromes: Relevance to Clinical Radiotherapy of Radioresistant Cancer", I. J. Radiation Oncology, Biology, Physics, vol. 27, No. 4, pp. 907–914, 1993.

Yosh Maruyama, M.D., FACR, et al., "Californium–252 Neutron Brachytherapy", From Nag S (ed): Principles and Practice of Brachytherapy, pp. 649–687, 1997.

J.C. Yanch, et al., "Dosimetry of $^{252}$Cf Sources for Neutron Radiotherapy with and without Augmentation by Boron Neutron Capture Therapy", Radiation Research, 131, pp. 249–256, 1992.

Roy A. Patchell, M.D., et al., "Postoperative Radiotherapy in the Treatment of Single Metastases to the Brain," JAMA, vol. 280, No. 17, pp. 1485–1489, Nov. 1998.

Jeffrey A. Coderr, et al., Review, "The Radiation Biology of Boron Neutron Capture Therapy", Radiation Research, 151, pp. 1–18, 1999.

Darrel D. Joel, et al., "Effect of dose and infusion time on the delivery of p–boronophenylolanine for neutron capture therapy", Journal of Neuro–Oncology 41, pp. 213–221, 1999.

J.G. Wierzbicki, et al., Measurement of augmentation of $^{252}$Cf implant by $^{10}$B and $^{157}$Gd neutron capture, Med. Phys., 21 (6), pp. 787–790, Jun. 1994.

* cited by examiner

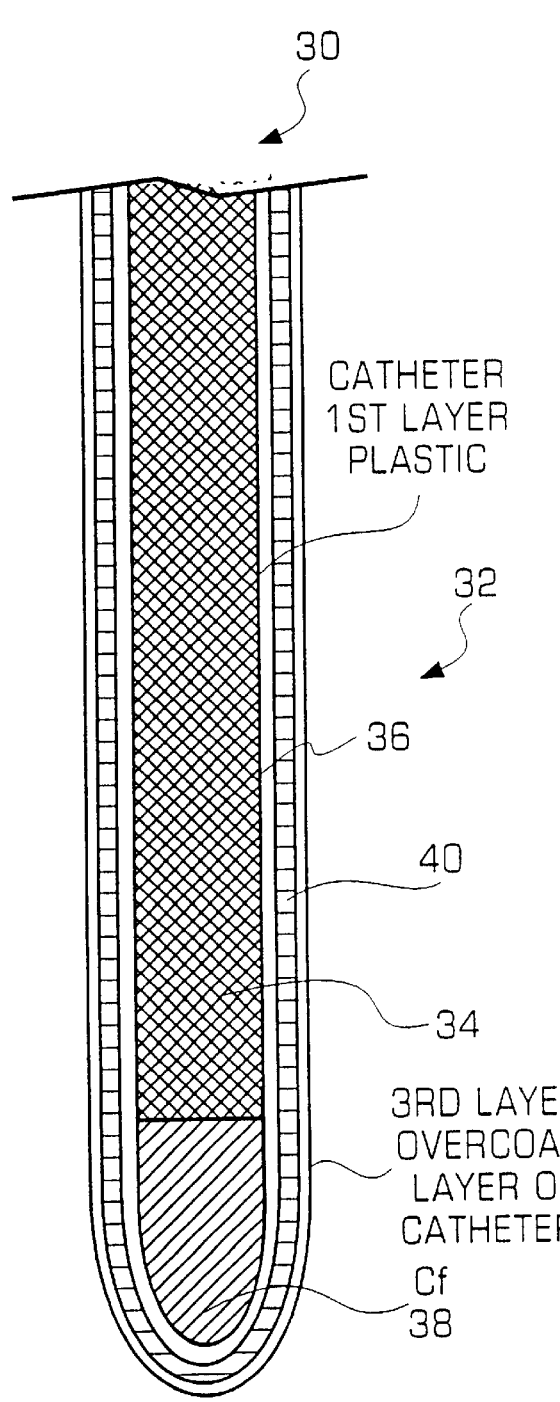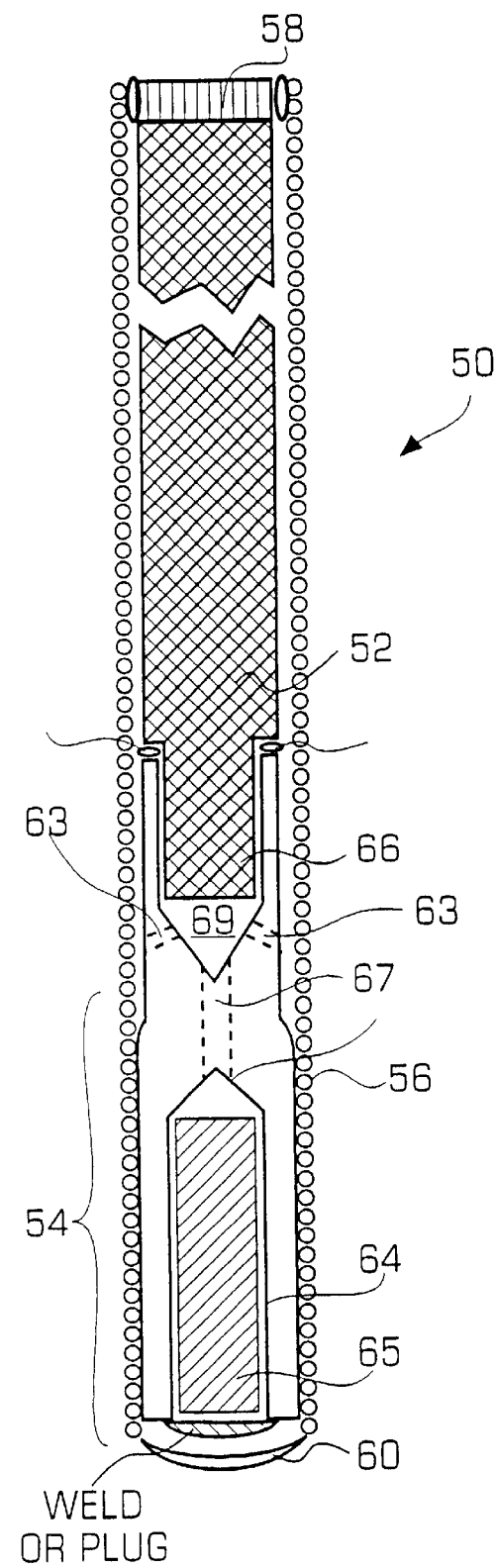
FIGURE 3
FIGURE 4

THE NEUTRON ENERGY SPECTRUM OF $^{252}$CF
described by $p(E) = C\exp(-E/a)\mathrm{Sinh}(bE)^{1/2}$
where a =1.025, b=2.926

All the units for E, a, and b are in MeV.

Note that: $\int_0^\infty p(E)dE = 1$

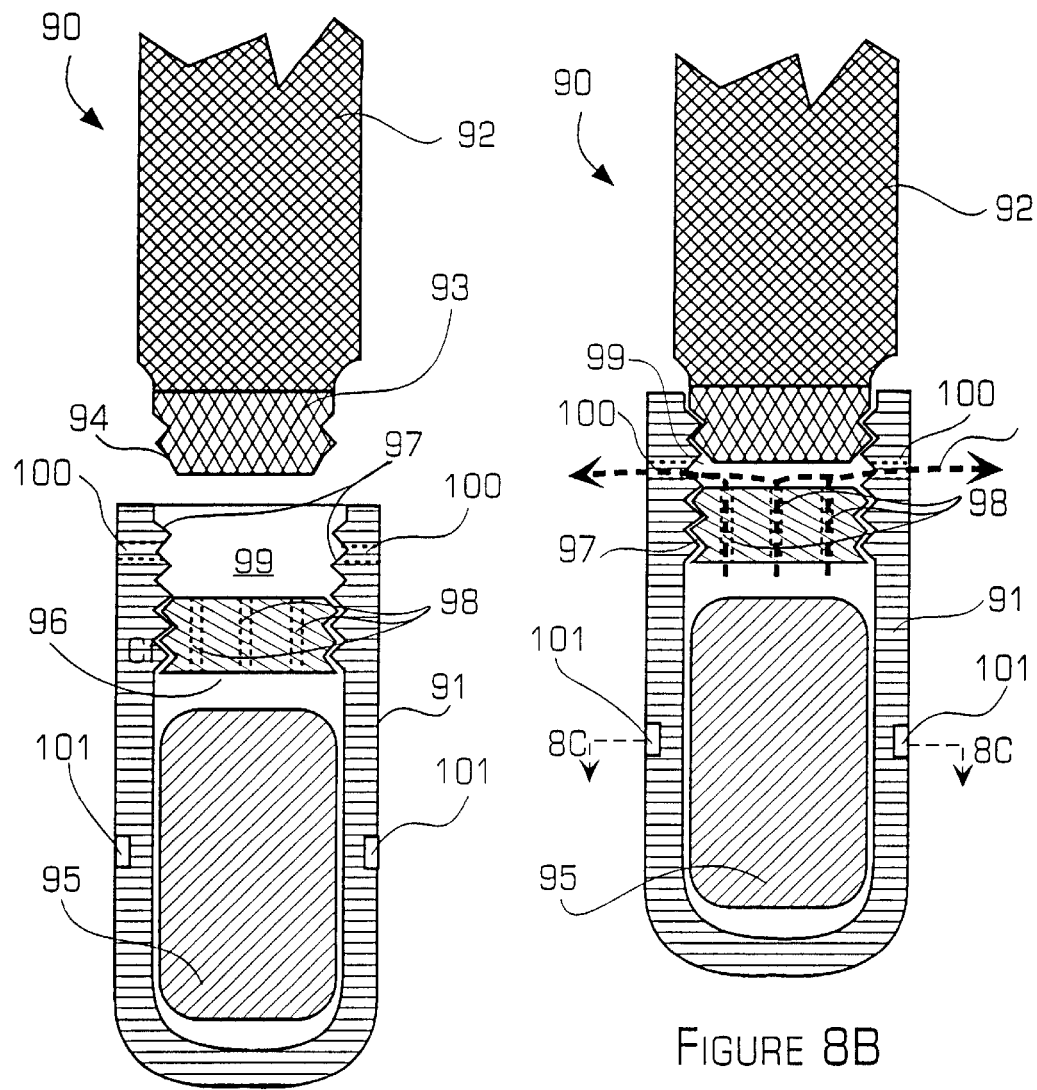
FIGURE 8A
FIGURE 8B
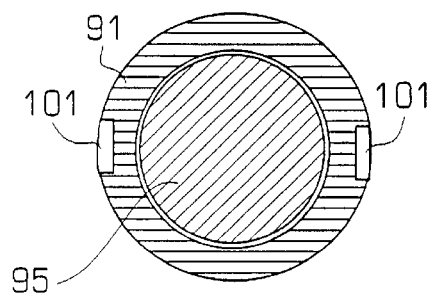
FIGURE 8C

NEUTRON BRACHYTHERAPY DEVICE AND METHOD

This application is a continuation, under 35 USC §120, of U.S. application Ser. No. 09/395,324 filed on Sep. 13, 1999, which is now U.S. Pat. No. 6,352,500.

BACKGROUND OF THE INVENTION

This invention relates generally to a device and method for generating particles and electromagnetic radiation that may be used for treating a variety of disorders, such as cancer, tumors and the like and in particular, to a device and method for utilizing neutrons to kill or damage tumor cells within the body of a patient.

There are various diseases in which undesirable cells grow within the body of a patient. These diseases include various types of cancers and other diseases in which a large mass of undesirable cells are formed in the body of the patient. To effectively treat these types of diseases, it is desirable to surgically remove as many of the undesirable cells as possible and then attempt by other means to damage or kill the cells remaining after the surgery. The most insidious of these diseases is cancer in which cells multiply uncontrollably in the body causing pain and the eventual death of the patient.

There are some forms of cancer which are particularly deadly in that they spread very rapidly, are located in places that make it difficult to operate and remove them and/or are nearly always fatal to the patient. One of these particularly deadly forms of cancer is a brain tumor. A brain tumor, once diagnosed, may typically kill the patient within a very short time frame. The five-year survival rate after the diagnosis of glioblastoma multiforme (one of the most frequent malignant brain tumor type) is less than 1%. Therefore, it is desirable to be able to extend the life expectancy of a person with a brain tumor and to improve the quality of life of the patient during the remaining time in his/her life. Many different treatments for various cancers, including brain tumors, have been developed that attempt to reduce the size of the tumor or eliminate the tumor entirely.

The treatment of these cancers may be conducted using non-radiation types of treatments. For example, chemotherapy may be used in which toxic chemicals are targeted at the cancer or tumor cells (using various well known techniques to target the tumor or cancer cells) so that the cancer or tumor cells are damaged or killed by the toxic chemicals. The problem with chemotherapy is that the toxic chemicals also tend to damage other cells or organ systems in the body, and have undesirable side effects, such as nausea, vomiting etc., which lead to a poor quality of life of the patient. For a brain tumor, the treatment typically involves surgery to debulk the tumor (remove as much of the tumor as possible without causing further damage to the healthy cells) followed by some other treatment to combat the cells remaining in the brain after the surgery. The treatment after the surgery may include various types of radiation treatment, as described below, which attempt to kill or damage the remaining cancer or tumor cells. The problem with this surgery and radiation treatment approach is that some brain tumors are inoperable and the radiation treatment alone does not sufficiently combat the tumor. Due to these limitations, other radiation or particle emitting treatments have been developed.

In the past, various types of radiation and particle emitting devices have been used for treating various diseases and maladies. The purpose of these devices is to destroy or disable the undesirable cells, such as tumor cells or cancer cells. To destroy or damage the undesirable cells, the particles or electromagnetic energy may strike and break the chemical bonds within the cancer cells so that these cells are destroyed. In any case, the radiation or particle energy must be highly focused on the tumor or cancer cells because the healthy cells surrounding the tumor or cancer cells are equally susceptible to radiation or particle damage. The goal, therefore, is to damage the cancer to tumor cells sufficiently with the radiation or particle energy to cause cell death while limiting the exposure of the healthy cells to the damaging particles and radiation. In particular, typical cells can repair some particle or radiation damage. Thus, the healthy cells with a more limited exposure than the tumor can repair the damage while the tumor or cancer cells cease functioning or die since they have been exposed to a larger dose of radiation or particles.

One typical technique for treating cancer or tumor cells is radiation treatment in which electromagnetic radiation is directed towards the tumor or cancer cells in order to damage the tumor or cancer cells. The radiation may be x-rays or other types of electromagnetic energy. The radiation is typically generated by a source outside the body, passes through the skin and tissue surrounding the tumor or cancer cells and is focused on the tumor or cancer cells so that a majority of the radiation energy is focused on the tumor or cancer cells. The problem with radiation treatment is that, to treat tumor or cancer cells inside of the body, the radiation must pass through surrounding healthy tissue which needs to be protected as much as possible from the radiation damage. Therefore, the amount of radiation energy that can be directed at the tumor cells during each treatment is limited by the amount of radiation that the surrounding healthy cells may be exposed to during each treatment. For example, if the dose to the surrounding healthy cells is too high, the healthy cells will also die which is undesirable. In addition, after a radiation treatment, the healthy surrounding cells must be given a chance to repair the damage before any further radiation treatment occurs. Therefore, due to the limited amount of radiation that may be directed to the tumor or cancer cells during each treatment and the period of time between each treatment to permit the healthy cells to repair, radiation treatments are delivered over many weeks. Thus, radiation treatment requires quite some time to damage the tumor or cancer cells sufficiently to kill them and may still cause a fair amount of damage to the surrounding healthy cells since the radiation must pass through the surrounding healthy cells.

Another typical technique for treating tumor or cancer cells is to use brachytherapy treatment in which a radiation source is inserted into or near the tumor so that the radiation from the radiation source is more focused into the tumor cells with less damage to the surrounding healthy cells. The radiation sources may include various elements that emit various types of radiation or particles including beta particles and gamma photons. Gamma photons and beta particles are referred to as low linear-energy-transfer (LET) radiation particles in which a particle transfers a small amount of its energy to a tumor cell on each passage. To be effective on cell killing, the small amount of energy transferred to each cell must be converted to free radicals via interacting with the oxygen existing in the cell. Therefore, a low LET radiation treatment is naturally ineffective to cancer cells that are hypoxic (have less oxygen than typical healthy cells). One type of hypoxic tumor cells are found in brain tumors.

Instead of these low LET radiation, it is also possible to use high LET radiation sources, such as neutrons. See R. A.

Patchell et al., "A phase I trial of neutron brachytherapy for the treatment of malignant gliomas", *The British Journal of Radiology,* Vol. 70, pp. 1162–1168 (November 1997). These neutron sources emit neutrons (a helium nucleus) which interact with the tumor cells to kill or damage them. A high LET radiation particle typically deposits a large fraction of its energy to a cell on each passage, and its cell killing effect is not affected by the amount of oxygen that is in the cells. Therefore, a neutron treatment is equally effective in killing or damaging both normal tumor cells and hypoxic tumor cells. The neutron source may be a radioactive element, such as californium (Cf), that may be internally placed near the tumor cells (i.e. the brachytherapy source) or an external neutron beam produced by a nuclear reactor or proton/deuteron accelerator. In a neutron therapy, neutrons typically interact with the tumor cells by colliding with hydrogen nuclei. The recoil hydrogen protons (i.e. protons) then break chemical bonds of the essential molecules (e.g. DNA) in the tumor cell and cause the tumor cell to be damaged and die.

The problem with typical brachytherapy neutron sources is that, although they may be inserted into a patient's body, they are too large to be effectively used to treat patients. In particular, the large size of the source prevents the delivery of a desired neutron dose distribution within and around a tumor. The result is either an underdose to the tumor which renders the treatment ineffective, or an overdose to healthy tissues exemplified by the necrosis of the scalp and healthy brain tissues surrounding the tumor as noted in the article cited above. Another limitation with brachytherapy neutron sources is that the amount of californium that can be encapsulated in a source seed is too small so that the treatment time required is too long (~30 hours).

The problems with using an external neutron beam are that the beam is difficult to focus and that neutrons must past through healthy tissue to reach a tumor. These problems necessarily cause large unwanted doses of neutrons to the healthy tissues surrounding the tumor and thus limit the effectiveness of the treatment. In addition, either a nuclear reactor or an accelerator is much too expensive compared to conventional radiation sources.

There is yet another way of using neutrons to treat cancers, the so-called boron neutron capture therapy (BNCT). During a BNCT treatment, a compound containing boron-10 is injected into the patient's bloodstream. Due to particular characteristics of the tumor cells, the boron compound is absorbed in greater amounts by the tumor cells than by the healthy cells surrounding the tumor. Then, the part of patient's body that contains the tumor is exposed to an external low-energy (epithermal) neutron beam generated by a nuclear reactor (or an accelerator). The neutrons further slow down and reach thermal equilibrium in tissue. The "thermal" neutrons then interact with the boron-10 in the tumor cells to cause damage. That is, the capture of a thermal neutron by a boron-10 nucleus in a tumor cell instantaneously produces two energetic ions (a lithium ion and a helium ion). The two ions, in turn, break the chemical bonds of the essential molecules (e.g. DNA) and cause damage to the tumor cell. The problems of the BNCT are that equal amount of the boron compounds do not enter each tumor cell and that the boron content in tumor cells during a treatment cannot be determined accurately. Therefore, it is impossible to know precisely the neutron fluence necessary to kill the tumor cells. In addition, an epithermal neutron beam produces a thermal neutron field having its flux peaks at a depth between 2 to 5 cm in tissue. Therefore, it becomes less effective in treating deep seated tumors.

To overcome the above limitations and problems of conventional cancer and tumor treatments and devices, it is desirable to provide a new neutron brachytherapy device and method. It is to this end that the present invention is directed.

SUMMARY OF THE INVENTION

In accordance with the invention, a neutron brachytherapy device and method are provided which preferably use californium ($^{252}$Cf) as the source to deliver neutrons directly to the tumor cells with minimal irradiation or damage to the healthy cells surrounding the tumor. A neutron from the source strikes the tumor cells and interact with the hydrogen in the cells to produce a charged hydrogen nucleus known as a recoil proton. The recoil proton then breaks chemical bonds of essential molecules (e.g. DNA) in the tumor cells and cause damages or deaths to the cells. The neutron source may be used alone or in combination with other treatments including, for example, boron neutron capture therapy (BNCT), surgery and conventional radiation treatments. The neutron source may be used to perform interstitial brachytherapy on tumors such as those occurring in the brain which generally have not responded to systemic therapy treatments. The neutron source in accordance with the invention has a higher radioactivity than the previously available neutron sources so that the total treatment time is significantly reduced. The neutron source in accordance with the invention also has a smaller size than the previously available neutron sources. The smaller size of the new source allows multiple sources to be more uniformly delivered and distributed within and around a tumor, and therefore provides more desirable dose distributions than the previously available sources.

The neutron source in accordance with the invention may include a neutron emitting radioactive material, such as Californium ($^{252}$Cf) in a preferred embodiment, encased within a capsule. The capsule in accordance with the invention may permit the helium gas generated as the neutron source decays to be dissipated so that the capsule does not need to be periodically processed to release the helium gas. The capsule may be welded onto a guide wire to form a source wire so that the source wire and capsule may be inserted into the patient. The capsule may be a single or double walled design. The neutron emitting material may be loaded into the source wire in various ways as described below. The guide wire in accordance with the invention may be braided to strengthen and increase the flexibility of the source wire as well as to prevent the source wire from kinking.

To insert the neutron source into the patient, a catheter with a closed distal end may be inserted into the tumor by a surgeon using various techniques, such as stereotactic visualization and the like, to place the catheter. The closed end catheter prevents the patient's fluids from contaminating the source wire. In accordance with the invention, there may be multiple catheters placed into the tumor depending on the dose distribution of the sources as well as the size and shape of the tumor. The catheters in accordance with the invention may be made of a flexible natural or synthetic material conventionally used in catheter manufacturing that is surrounded by a coiled metal wire. This prevents the catheter and source wire in the catheter from kinking and becoming lodged in the patient and increases the strength of the catheter. The metal coiled wire layer may be coiled around the catheter because the metal in the coiled wire does not affect the operation of the neutron source, whereas the operation of typical low LET radiation sources would be significantly affected by the metal coil wrapped around them. Once the catheters are placed in the appropriate locations in the tumor, a test wire without a radiation source is inserted into each catheter via a computer controlled remote delivery system called an "afterloader" to ensure the source delivering process and then the test wire is removed. If successful, the source wire with the neutron source for each catheter is then loaded into each catheter to carry out the treatment.

Thus, in accordance with the invention, a neutron source for performing interstitial neutron brachytherapy is provided wherein the neutron source comprises a neutron emitting source material that is radioactive and decays while releasing helium gas and generating neutrons during the decay. The neutron source further comprises a capsule within which the neutron emitting source material is enclosed. The capsule walls do not interfere with the source neutrons and the capsule is sufficiently small so that multiple capsules can be simultaneously inserted into the body of a patient to treat the tumor. The neutron source further comprises a guide wire affixed to the capsule wherein the guide wire controlling the positioning of the capsule within the patient.

BRIEF DESCRIPTION OF THE DRAWINGS

FIG. 3 is a diagram illustrating an example of a source wire in accordance with the invention;

FIG. 4 is a diagram illustrating a first embodiment of a neutron source in accordance with the invention;

FIGS. 8A, 8B and 8C are diagrams illustrating a neutron source in accordance with the invention wherein no welding of the capsule is required;

DETAILED DESCRIPTION OF A PREFERRED EMBODIMENT

The invention is particularly applicable to treating brain tumors and it is in this context that the invention will be described. It will be appreciated, however, that the device and method in accordance with the invention has greater utility, such as to treating other types of cancers and tumors and for other types of interstitial brachytherapy.

Figure 1:
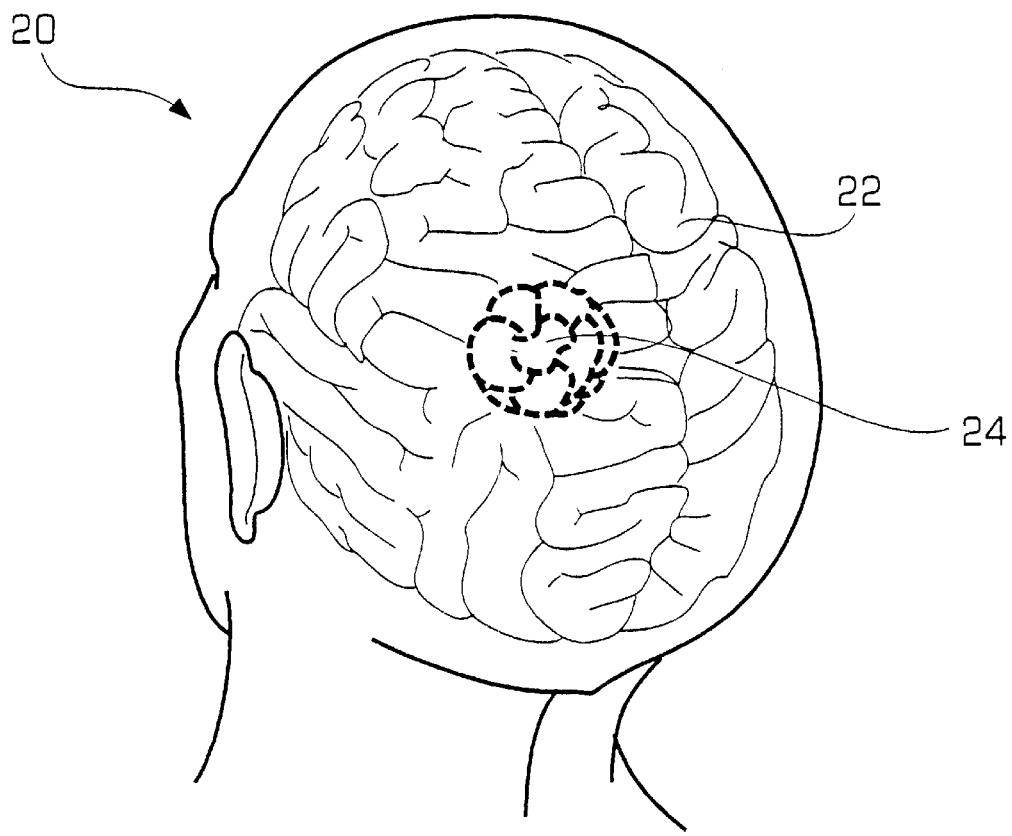
FIG. 1 is a diagram illustrating a patient with a brain tumor that may be treated using the neutron brachytherapy device in accordance with the invention.

FIG. 1 is a diagram illustrating a patient's head 20. The diagram shows the patient's brain 22 with a deep seated tumor 24 that may be treated using the neutron brachytherapy device in accordance with the invention. In one typical treatment, the surgeon may surgically remove a majority of the tumor, known as tumor debulking. The neutron brachytherapy device in accordance with the invention may then be used to kill the remaining tumor cells (typically on the periphery of the tumor) instead of a conventional radiation or chemotherapy treatment. The neutron brachytherapy device reduces the damage to the surrounding healthy cells so that the amount of killing effect that can be applied to the tumor cells is increased without the undesirable side effects of the conventional radiation or chemotherapy treatments. The neutron therapy using the neutron brachytherapy device in accordance with the invention may also be combined with other treatment modalities such as boron neutron capture therapy (BNCT).

In some situations, the tumor, due to its size or location in the brain, is inoperable so that the patient is typically left to radiation or chemotherapy treatments. These treatments do not adequately treat the tumor cells since some brain tumors, such as a glioblastoma multiforme, often contain hypoxic cells that do not respond to the conventional radiation or chemotherapy treatments. The neutron brachytherapy device in accordance with the invention may be used to shrink the previously inoperable tumor sufficiently so that the tumor may then be removed or debulked by the surgeon during a surgical procedure. In this situation, the neutron brachytherapy device may also be used after the debulking procedure to kill the tumor cells remaining after the debulking procedure.

The neutron brachytherapy device in accordance with the invention generates fast neutrons at energy levels of about 1–5 MeV of energy. The neutrons exiting the neutron brachytherapy source strike hydrogen atoms in the tumor cells, and the resulting charged hydrogen nuclei (i.e. recoil protons) are capable of breaking chemical bonds of essential molecules (e.g. DNA) in the tumor cell and thus damage or kill the tumor cell. In this manner, the neutron brachytherapy device kills the tumor cells via the recoil protons produced by the elastic collisions between the source neutrons and the hydrogen nuclei in tissue. Now, the operation of the neutron brachytherapy device in accordance with the invention will be described.

Figure 2:
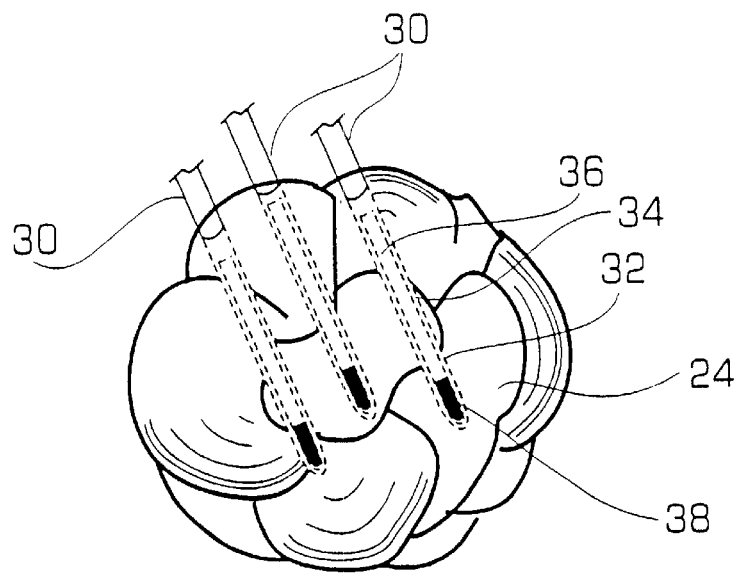
FIG. 2 is a diagram illustrating one or more neutron sources in accordance with the invention placed in a tumor to kill or damage the tumor cells.

FIG. 2 is a diagram illustrating an example of one or more neutron brachytherapy devices 30 in accordance with the invention placed in the tumor 24 to kill or damage the tumor cells. For purposes of illustration only, the tumor 24 is shown without the surrounding healthy brain cells. In this example, there are three neutron brachytherapy devices inserted into the tumor cells based on the size and shape of the tumor as well as the dose distribution of each of the neutron sources. The number of neutron sources inserted into the tumor in accordance with the invention may be varied. As shown, each neutron brachytherapy device 30 may include a hollow catheter 32 with a closed end that has been inserted into a predetermined portion of the tumor by the surgeon. A source wire 34 may fit within the catheter and is inserted into the catheter by a computer-controlled remote afterloader system. The source wire 34 may include a guide wire 36 and a neutron source capsule 38 that may be attached to the end of the guide wire. The neutron source capsule may contain the neutron generating material, that may be $Cf^{252}$ in a preferred embodiment. The neutron generating material may radioactively decay to generate helium gas and the neutrons that indirectly damage the tumor cells. The neutron sources may be left in the tumor for about 1–5 hours to complete the treatment. Once the treatment has been completed, the brachytherapy devices 30 and the catheters may be removed from the tumor and the entry points for the catheters in the patient are sewn up. Now, the source wire and guide wire in accordance with the invention will be described in more detail.

FIG. 3 is a diagram illustrating an example of the brachytherapy device 30 in accordance with the invention. In this example, the catheter 32 and the source wire 34 that fits into the catheter are shown. To prevent an accident, such as the source piercing the end of the catheter and coming in contact with the patient, the end of the radiation material 38 may be rounded. The catheter 32 with the closed end ensures that the source wire never comes into contact with the fluids of the patient so that the source wire may be used for multiple patients without cleaning the source wire. A neutron source wire is very difficult to clean since it must be done in a radiation hot cell to prevent neutron exposure. To maintain the flexibility of the source wire and catheter (so that the catheter may be positioned in difficult locations) while increasing the safety of the neutron brachytherapy device, the device 30 may include a metallic wire 40 coiled around one layer of the catheter. The coiled wire increases the strength of the source wire, permits the source wire and catheter to be bent to get to difficult locations and prevents the source wire and catheter from becoming kinked. A kinked catheter or source wire might cause the neutron source 38 to be stuck within the patient so that the patient receives an unwanted dose of neutrons. Now, a first embodiment of the neutron source in accordance with the invention will be described.

FIG. 4 is a diagram illustrating a first embodiment of a neutron source wire 50 in accordance with the invention. The neutron source wire may be attached to a guide wire or cable 52 and may include a neutron source 54 attached to the tip of the guide wire or cable 52. The guide wire and the neutron source may be surrounded by a coiled wire 56 that acts as a spring increasing the flexibility and strength of the neutron source wire and prevents the neutron source wire from kinking so that the neutron source is less likely to be stuck within the patient. In accordance with the invention, the guide wire may be a braided wire as described below with reference to FIGS. 6A–6C or may be made of a single nitinol material wire that also may be surrounded by a coiled wire. The coiled wire 56 may be securely attached to the guide wire or cable 52 by a weld 58 at an end opposite from the source. In a preferred embodiment, the coiled wire may be metallic since metal does not affect the effectiveness of the neutrons. In a preferred embodiment, the source wire, including the neutron source and the guide wire, may be approximately four to ten feet long. To ensure that the source wire 50 does not perforate the end of a catheter and contaminate the patient and the neutron source, the neutron source 54 may include a rounded ball end 60.

The neutron source 54 may include a source capsule 64 containing a neutron source material 65. The capsule carrier may include a circular hole 66 at its bottom into which the guide wire 52 may be placed. The capsule carrier and the guide wire may then be rigidly attached together, such as by welding in a preferred embodiment. The neutron source 54 may further include one or more vent holes 63 to allow the helium gas to escape the capsule and prevent a pressure build-up over time in the capsule. A first hole 67 connects the neutron source material 65 to a gas compartment 69 formed near the end of the guide wire 52. The other holes allow the helium gas to escape from the gas compartment 69 to the atmosphere in order to release the pressure.

Figure 5:
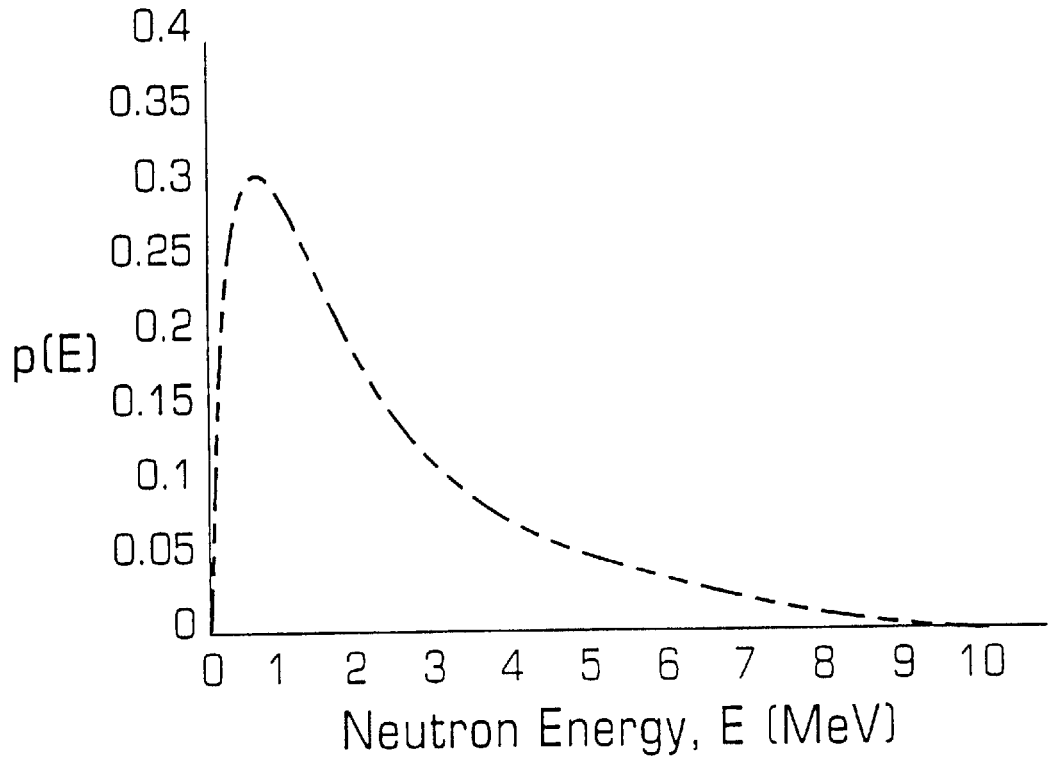
FIG. 5 is a chart illustrating the energy spectrum of the Californium radioactive material.

The neutron source material in accordance with a preferred embodiment of the invention may be an radioactive element from the periodic table known as californium ($Cf^{252}$). Californium has a half-life of about 2.6 years. A majority (97%) of the decay of Californium produces helium gas (alpha particles), but the decay also produces neutrons. The neutron energy spectrum of the Californium used in the preferred embodiment is shown in FIG. 5. Notice that the peak of the neutron energies occurs between about 1 MeV and 5 MeV.

The neutron source material may be formed using various different techniques and certain materials as described in a paper entitled, "Development of High-activity $^{252}Cf$ Sources for Neutron Brachytherapy" by R. C. Martin et al., *Appl. Radiat. Isot.*, Vol. 48, No. 10–12, pp. 1567–1570 (1997). To produce the neutron sources, a heavily shielded hot cell must be used. Palladium (Pd) may be deposited onto a fine precipitate of californium oxalate, $Cf_2(C_2O_4)$, in an aqueous solution. The Pd-coated particles may then be dried, calcined to Pd-coated $Cf_2O_3$, pressed into a pellet at 50% of the desired density, sintered at a predetermined temperature at about 1300 degrees, pressed again to 90% of the desired density and then pressed into a capsule of platinum-iridium alloy. In accordance with the invention, the source capsule may preferably be 0.5–2 mm in outside diameter, that is comparable to other beta and gamma brachytherapy sources and may preferably be 3–6 mm long. The preferred nominal intensity of the neutron source in accordance with the invention may be $1.0 \times 10^9$ neutrons per second. In fact, in accordance with the invention, the amount of Californium in the source wire may vary between 100 $\mu$g and 1 mg. For a 1 mg source wire, the intensity is $2.3 \times 10^9$ neutrons per second. In accordance with the invention, the neutron source may be 50 times smaller than typical neutron sources and 10 times more radioactivity which permits shorter treatment times. Now, a method for making the braided guide wire in accordance with the invention will be described.

Figure 6A:
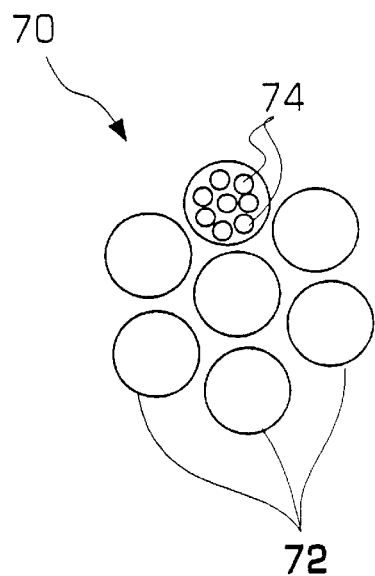
FIGS. 6A–6C are diagrams illustrating the braided guide wire in accordance with the invention.
Figure 6B:
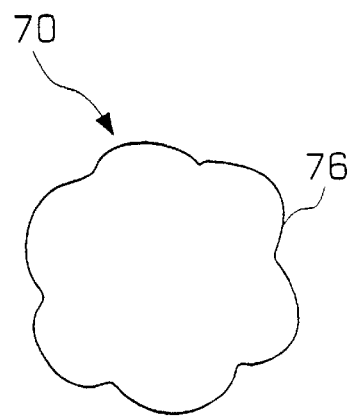
Figure 6C:
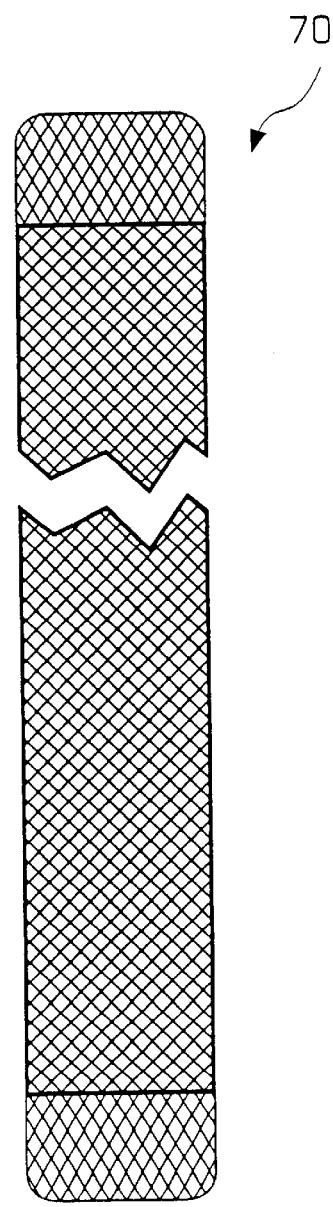

FIGS. 6A–6C are diagrams illustrating the braided guide wire 70 in accordance with the invention. As shown in FIG. 6A, the braided guide wire may include a bundle of 7 bundles of wires 72 and each bundle of wire 72 may also be braided with seven single wires 74. Thus, the braided guide wire may be formed with a 7×7 bundle of braided wires to increase the strength and flexibility of the guide wire. The problem with the 7×7 bundle, as shown in FIG. 6B, is that an outer surface 76 of the bundle is uneven due to the bundle of braided wires. The problem is that the uneven surface may perforate the catheter into which it is inserted or make is difficult to push the guide wire through the catheter. This problem can be remedied by swaging the bundle of wires. In accordance with the invention, as shown in FIG. 6C, the tips of the various wires may be fused together and rounded and then the tips of the guide wire may be ground down so that the resultant surface of the guide wire is smooth. Thus, in accordance with the invention, the guide wire may have the flexibility and strength associated with a braided wire, but the smoothness normally associated with a single wire. Now, a second embodiment of the neutron source will be described.

Figure 7A:
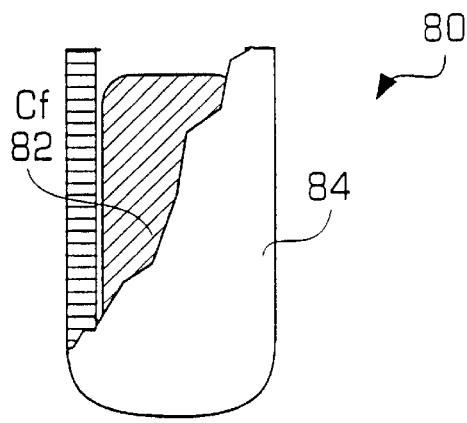
FIGS. 7A–7C are diagrams illustrating a second embodiment of the neutron source in accordance with the invention.
Figure 7B:
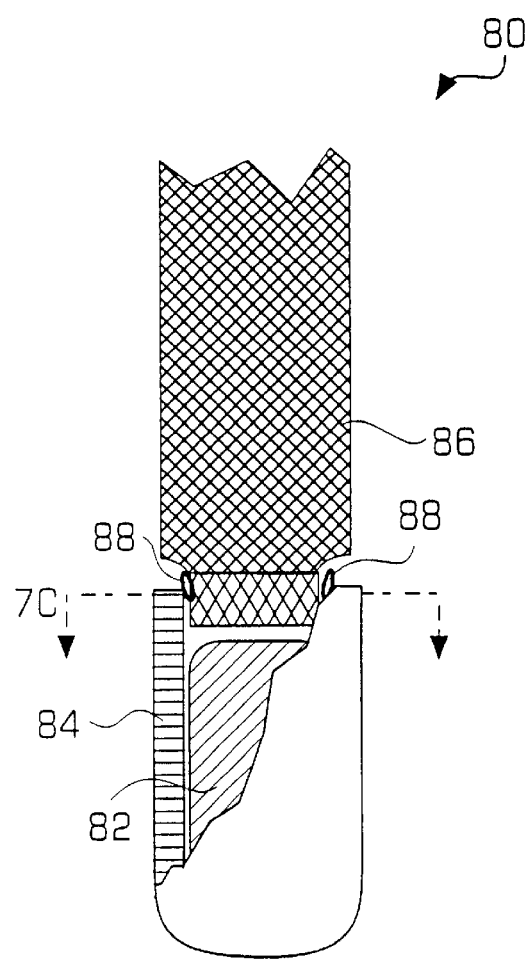
Figure 7C:
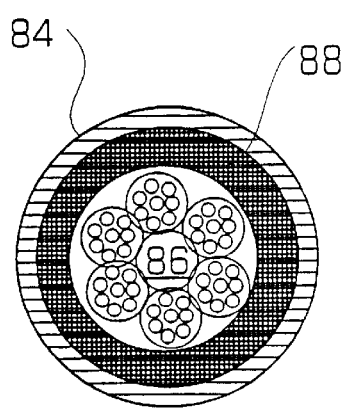

FIGS. 7A–7C are diagrams illustrating a second embodiment of the neutron source 50 in accordance with the invention. First, as shown in FIG. 7A, a neutron capsule 80 may be formed by placing a neutron emitting material 82, such as californium in a preferred embodiment, into a capsule casing 84. Since the neutron emitting material is exposed during the neutron source production in this embodiment, the neutron source must be produced in a heavily shielded hot cell. As shown in FIG. 7B, a smooth braided guide wire (swaged with finished ends as above) 86 may be inserted into the opening in the capsule casing and a weld 88 may be formed around the top of the capsule casing and the guide wire to secure the guide wire to the capsule and seal the neutron emitting material into the capsule. An end view of the weld is shown in FIG. 7C. Vent holes may also be added in this design. Now, a third embodiment of the neutron source in accordance with the invention will be described.

FIGS. 8A, 8B and 8C illustrate an embodiment of a neutron source wire 90 in which a capsule 91 does not need to be welded onto a guide wire 92. The advantage is that there is no possibility of a weld fatiguing and breaking so that the reliability and safety of the neutron source wire 90 is increased. In this embodiment, an end 93 of the guide wire 92 that fits into the capsule 91 may be fused and ground as described above and may be threaded so that it may be threaded into the capsule as described below. The guide wire may also have a tapered section 94 so that there is space between a neutron source 95 and the guide wire into which helium gas may build up when the neutron source wire is assembled as shown in FIG. 8B.

The capsule 91 may include the neutron source 95 which is loaded into the open end of the capsule and a threaded plug 96 (it may also be a slotted headless threaded screw). The walls of the capsule may include a threaded section 97. The threaded section 97 begins above the top of the neutron source 95 so that the neutron source can not be contacted by the plug 96 and possibly damaged. The threaded plug 96 may be aligned with the threads 97 in the capsule walls and screwed into the capsule until the plug fits snugly above the neutron source. The slotted portion of the plug may be used to screw the plug down towards the neutron source. The plug 96 may include one or more vent holes 98 that permit any helium gas generated by the neutron source to escape into a gas compartment 99 formed between the tapered end 94 of the guide wire and the plug 96. The walls of the capsule 91 may further include one or more vent holes 100 adjacent to the gas compartment so that any gas in the gas compartment may pass through the vent holes 100 into the atmosphere. The capsule 91 may further include one or more relief flats 101 (as shown in more detail in FIG. 8B) that permit the capsule 91 to be held while the plug 96 and the guide wire 92 are screwed into the capsule. The assembled neutron source wire 90 is shown in FIG. 9B. In one variation of this embodiment, the relief flats 101 may coincide with the vent holes 100 in the capsule to allow the helium gas to escape the capsule and vent to the outside. In accordance with another variation, the entire source wire 90 may also be placed inside an outer coiled wire to provide an additional safety factor as described above. Now, an embodiment for loading a neutron source will be described.

Figure 9A:
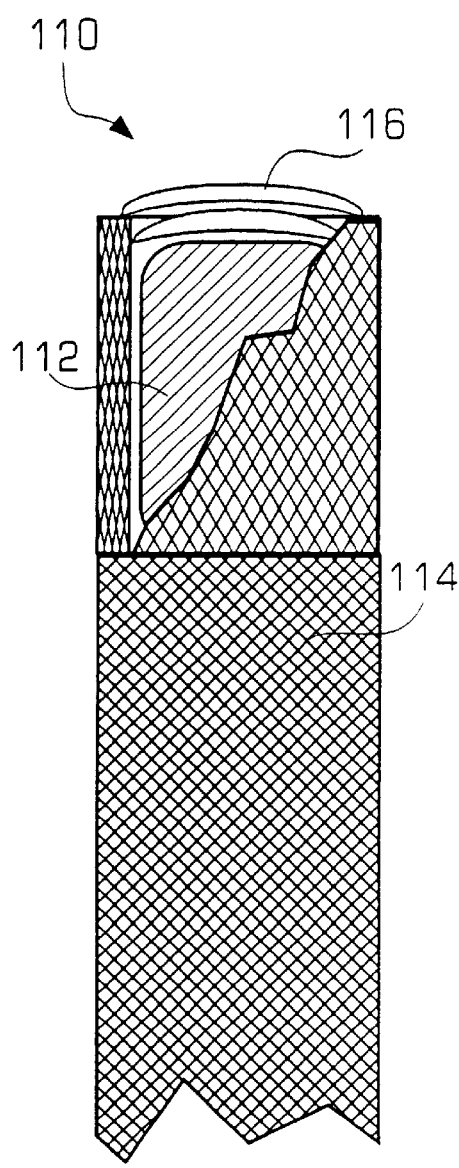
FIGS. 9A and 9B are diagrams illustrating two embodiments of the loading of the neutron emitting material in accordance with the invention.
Figure 9B:
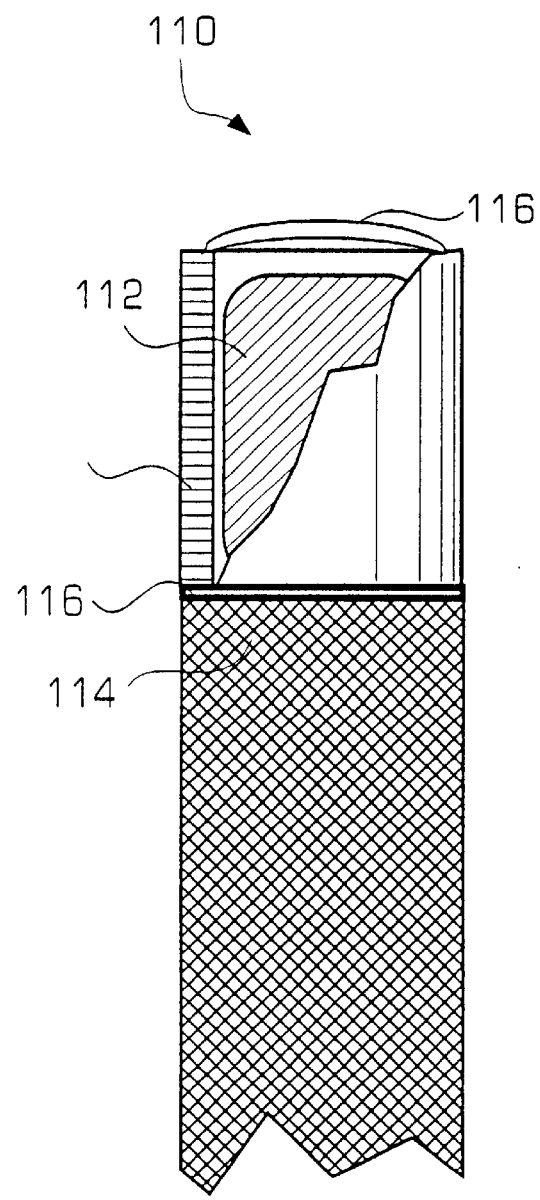

FIG. 9A is a diagram illustrating an embodiment for loading a neutron source 110 in accordance with the invention. In particular, the next several diagrams illustrate different techniques for encapsulating the neutron emitting material in a capsule in accordance with the invention. In the embodiment shown in FIG. 9A, the neutron emitting material 112 is formed into a pellet and a hole is formed in the end of a guide wire 114 so that the neutron emitting material may be placed into the end of the guide wire. Then, a weld 116 may be formed, using a typical welding system such as a laser welding system, around the neutron emitting material 112 on top of the tip of the guide wire. Note: the guide wire would be processed in the same fashion as mentioned above. In FIG. 9B, instead of drilling a hole in the end of the guide wire, a tube is welded onto one end of the guide wire. Note: the guide wire is also processed as mentioned above-swaged, fused & ground ends. In this embodiment, the process must be completed in a heavily shielded hot cell since the neutron emitting material is exposed. Now, another embodiment will be described.

Figure 10:
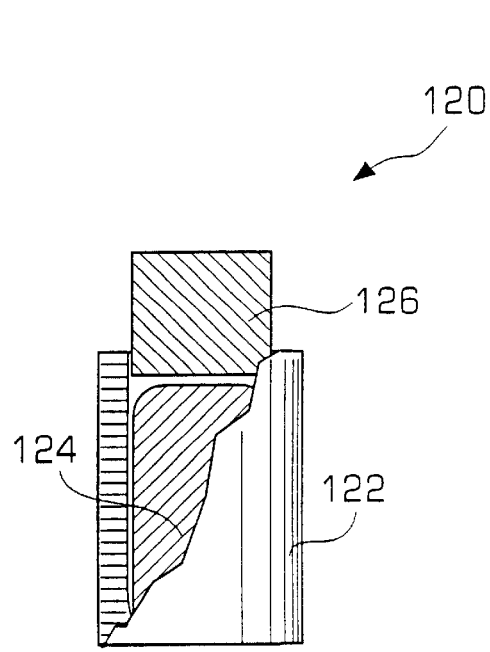
FIG. 10 is a diagram illustrating another embodiment of the loading of the neutron emitting material in accordance the invention.

FIG. 10 is a diagram illustrating another embodiment for loading a neutron source 120 in accordance with the invention wherein the source 120 may be formed in the heavily shielded hot cell and then may be removed from the hot cell to secure it to the guide wire. In particular, a bullet shaped capsule casing 122 is formed from a suitable material, such as stainless steel, and a neutron emitting source material 124 may be loaded in the bottom of the capsule casing. Next, a plug or seal 126 may be placed in or over the open end in the hot cell which seals the neutron emitting material inside the capsule. The seal 126 may be made out of a metal. Once the seal is installed, the entire neutron source 120 may be washed with acid to remove contaminants and any residual neutron emitting material. Then, the neutron source 120 may be removed from the hot cell and a guide wire (not shown) may be attached to the neutron source outside of the hot cell which makes the attachment of the guide wire to the neutron source easier. Now, an instrument used in the placement of the catheters in accordance with the invention will be described.

Figure 11:
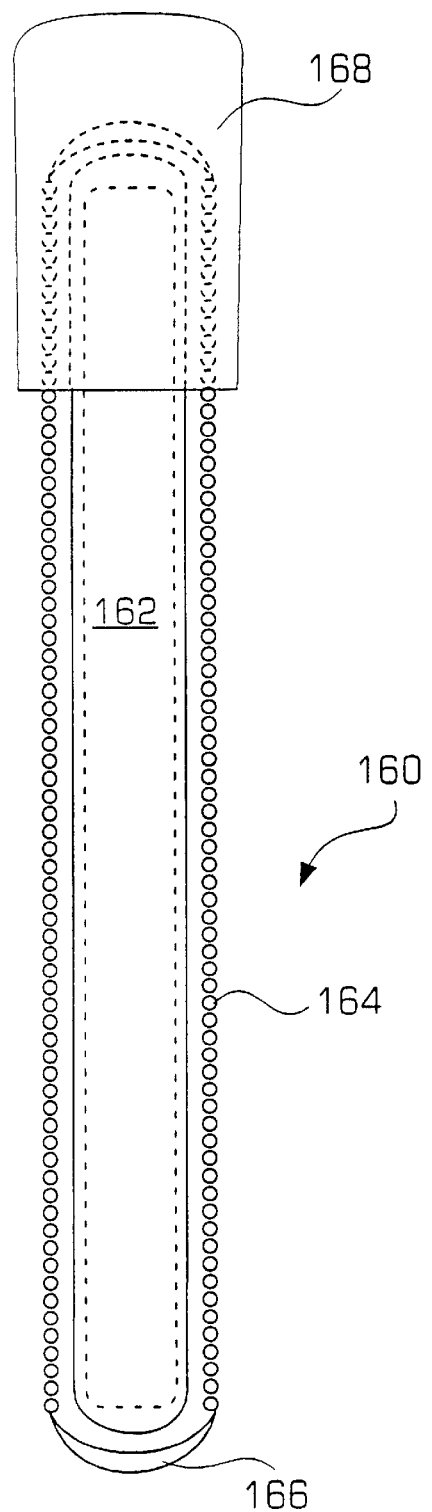
FIG. 11 is a diagram illustrating a coiled wire assembly in accordance with the invention.

FIG. 11 is a diagram illustrating a coiled wire assembly 160 in accordance with the invention. The outside diameter of the assembly is the same as the neutron source wire. It is significantly shorter in length (approximately 12–15 inches). The coiled assembly 160 may be inserted into a catheter before the catheter is inserted into the brain through a burr hole to maintain the rigidity of the catheter during its insertion. The coiled wire assembly may include a core 162 that may be wrapped by a coiled spring wire 164 to increase the flexibility and strength of the assembly. The coiled wire assembly is also less likely to be kinked. The coiled wire assembly 160 may also include a ball end tip 166 that prevents the coiled wire assembly from puncturing the tip of the closed end catheter during the insertion of the coiled wire assembly into the catheter. The coiled wire assembly may also include a handle portion 168 attached to the end of the coiled wire assembly opposite of the ball end tip so that the coiled wire assembly may be manipulated by a surgeon. Since this assembly is almost the same as the neutron source wire, it almost guarantees the source wire can be placed when using the remote controlled delivery system. Now, a single encapsulated neutron source in accordance with the invention will be described.

Figure 12:
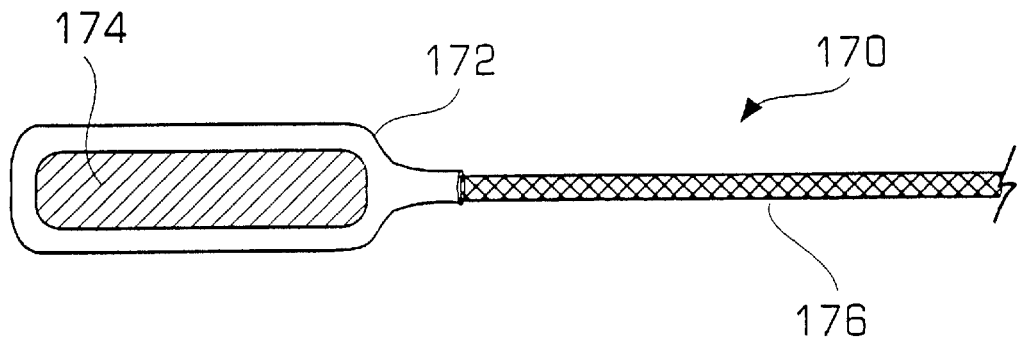
FIG. 12 is a diagram illustrating a single encapsulated source in accordance with the invention.

FIG. 12 is a diagram illustrating a single encapsulated source 170 in accordance with the invention. In this embodiment, a capsule 172 is formed as described above with a neutron emitting source material 174, such as Californium, inside of the capsule. To form the capsule, the capsule body is formed with an open end, the open end is pointed upwards, the neutron emitting material is loaded into the capsule through the open end, the open end is reshaped to contain the neutron emitting material in the capsule, the capsule is crimped over a wire 176. The capsule may then be welded onto the end of a braided guide wire 176 to form the neutron source wire. The single encapsulation requires only a single weld at the guide wire connection. The single encapsulation neutron source may preferably have an outside diameter of the cylindrical capsule of between 1.2–1.8 mm (and more preferably about 1.5 mm), an inner diameter of the capsule of between 1–1.3 mm (and more preferably about 1.1 mm) and a capsule wall thickness of between 0.005"–0.009" (and more preferably about 0.008"). Now, another single encapsulation embodiment will be described.

Figure 13:
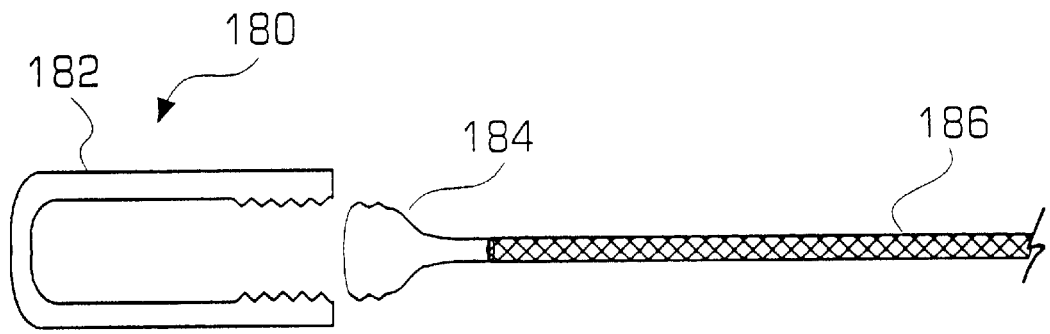
FIG. 13 is a diagram illustrating another embodiment of the single encapsulated source in accordance with the invention.

FIG. 13 is a diagram illustrating another embodiment of the single encapsulated neutron source 180 in accordance with the invention. In this embodiment, the neutron source may include a capsule (shell) 182 and a plug or cap piece 184 that may fit into the end of the capsule. In this embodiment, the neutron source material may be placed into the capsule. Then, the plug piece 184 may be mechanically fitted into the body piece to seal the neutron emitting material in the capsule. The capsule and plug piece may both also have corresponding screw threads so that the plug piece may be screwed into the body piece. Next, the capsule and the plug piece are welded together to ensure a tight seal. Next, a braided guide wire 186 may be welded into the plug piece to secure the neutron source capsule to the guide wire. The dimensions of this embodiment are approximately the same as the embodiment described above with reference to FIG. 12. Now, a double encapsulated neutron source in accordance with the invention will be described.

Figure 14:
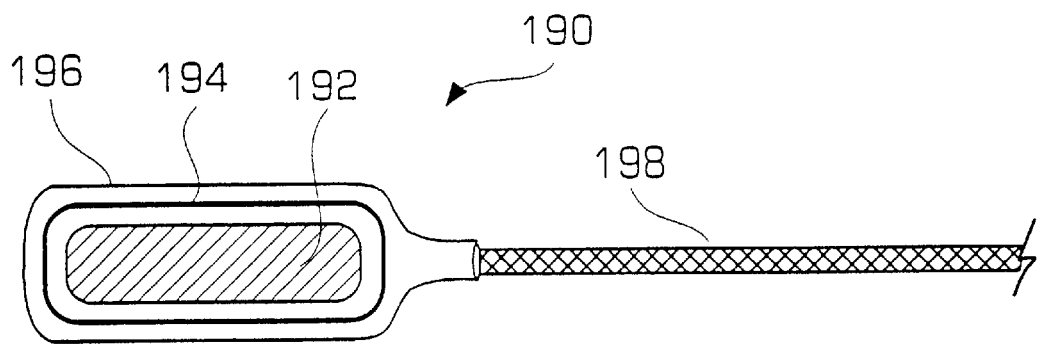
FIG. 14 is a diagram illustrating a double encapsulated source in accordance with the invention.

FIG. 14 is a diagram illustrating a double encapsulated neutron source 190 in accordance with the invention. The double encapsulated embodiment may include a neutron emitting source material 192 loaded into an inner capsule 194 and the inner capsule is sealed. The walls of the inner capsule may be permeable (e.g., made of a sputtered metal layer that is a few angstroms thick or made of a polymer) so that the helium gas generated by the neutron emitting source material may pass through the walls of the inner capsule to prevent unwanted gas build-up. The sealed inner capsule may then be placed within an outer capsule 196 and then the outer capsule may also be sealed. The outer capsule may also have permeable walls (as described above) so that the helium gas may also pass through the outer capsule and travel through the catheter to the outside world. Instead of using permeable walls for the capsules, each capsule may have vent holes which permit the gas to escape from within the capsule(s). The outer capsule may then be crimped onto a braided guide wire 198 and the guide wire may be welded to the outer capsule. In a preferred embodiment, the inner capsule may have an outer diameter of between 1–1.3 mm (and preferably about 1.15 mm), an inner diameter of between 0.6–1 mm (and preferably about 0.85 mm) and a wall thickness of between 0.005"–0.008" (and preferably about 0.006"). The outer capsule may preferably have an outer diameter of between 1.2–1.8 mm (and preferably about 1.5 mm), an inner diameter of 1–1.4 mm (and preferably about 1.25 mm) and a wall thickness of between 0.004"–0.007" (and preferably about 0.005"). In this embodiment, the neutron emitting source material may be sealed within two separate capsules to increase the safety of the neutron source.

While the foregoing has been with reference to a particular embodiment of the invention, it will be appreciated by those skilled in the art that changes in this embodiment may be made without departing from the principles and spirit of the invention, the scope of which is defined by the appended claims.

What is claimed is:

1. A neutron source for performing neutron brachytherapy, the neutron source comprising:
   a neutron emitting source material, the neutron emitting source material radioactively decaying and releasing helium gas and neutrons during the decay, wherein the neutron emitting source material has an intensity between about $2.3 \times 10^8$ to about $2.3 \times 10^9$ neutrons per sec.; and
   a capsule encapsulating the neutron emitting source material, the capsule having a cylindrical shape with an outer diameter less than about 2 mm.

2. The neutron source of claim 1, wherein the helium gas produced by the neutron emitting source material escapes through walls of the capsule so that the helium gas does not build-up in the capsule.

3. The neutron source of claim 2, wherein the walls of the capsule further comprise one or more vent holes in the walls of the capsule to permit the gas to escape from within the capsule.

4. The neutron source of claim 2, wherein the walls of the capsule further comprise a material that is permeable to the gas so that the gas passes through the walls.

5. The neutron source of claim 4, wherein the wall material comprises a sputtered layer of metal sufficiently thin to permit the gas to penetrate through the walls.

6. The neutron source of claim 4, wherein the wall material comprises a polymer material.

7. The neutron source of claim 1 further comprising a guide wire attached to the capsule for positioning the capsule, wherein the guide wire comprises a bundle of braided wires that are flexible and reduce kinking of the guide wire.

8. The neutron source of claim 7, wherein the bundle of guide wires further comprise a central braided wire surrounding by six braided wires, wherein a tip of the bundle of wires is rounded and an outer surface of the bundled wires is smoothed to form a smooth wire with the characteristics of a bundle of wires.

9. The neutron source of claim 1 further comprising a wire coiled around the capsule and the a guide wire to increase the strength and flexibility of the guide wire, prevent kinking of the guide wire and providing safety in that the coiled wire traps the capsule if it breaks off from the guide wire, the coiled wire not affecting the emission of the neutrons.

10. The neutron source of claim 1, wherein the capsule comprises a metallic casing having an open end into which the neutron emitting source material is loaded, the open end of the metallic casing being closed to seal the neutron emitting source material into the metallic casing and the a guide wire being permanently affixed onto the metallic casing.

11. The neutron source of claim 10, wherein the capsule further comprises a vent hole in a portion of the metallic casing to permit the helium gas generated by the decay of the neutron emitting source material to escape from the capsule so that gas pressure does not build-up in the capsule.

12. The neutron source of claim 1, wherein the capsule comprises a body portion and a cap portion, the body portion having an open end into which the neutron emitting source material is loaded, the body portion and the cap portion mechanically fitting together to seal the neutron emitting source material into the body portion.

13. The neutron source of claim 1, wherein the capsule comprises a body portion and a cap portion, the body portion having an open end into which the neutron emitting source material is loaded, the body portion and the cap portion having threads so that the body portion and the cap portion are screwed together to seal the neutron emitting source material into the body portion.

14. The neutron source of claim 13, wherein the capsule further comprises an inner capsule into which the neutron emitting source material is sealed and an outer capsule into which the inner capsule is sealed.

15. The neutron source of claim 1, wherein a guide wire comprises a nitinol wire.

16. The neutron source of claim 1 further comprises a closed end catheter into which the neutron source is placed in order to treat a patient, the closed end catheter prevents the neutron source from making contact with the patient's bodily fluids.

17. The neutron source of claim 16, wherein the closed end catheter further comprises a wire coiled around the catheter, the coiled wire not affecting the emission of the neutrons.

18. The neutron source of claim 1, wherein the capsule further comprises a source module comprising a wire having a central hole into which a pellet of neutron emitting source material is placed and a weld surrounding the pellet and securing the pellet to the wire.

19. The neutron source of claim 1, wherein the capsule further comprises a source module comprising a casing having an open end into which the neutron emitting source material is loaded and a seal formed over the neutron emitting source material to seal the neutron emitting source material into the casing.

20. The neutron source of claim 1, wherein the capsule further comprises a source module comprising a source casing having a first well and a second well opposite of the first well to form an H-shaped structure, the neutron emitting source material being loaded into the first well, a weld being formed over the first well to seal the neutron emitting source material into the first well, the a guide wire being inserted into the second well.

21. The neutron source of claim 1, wherein the neutron emitting source material comprises a predetermined amount of Californium-252, the predetermined amount being between about 100 $\mu$g and about 1 mg.

22. The neutron source of claim 1, wherein the capsule further comprises a casing having an inner threaded portion into which the neutron emitting source material is loaded, a threaded plug that screws into the inner threaded portion of the casing and a guide wire having a threaded end that screws into the casing above the plug to form a neutron source wire without welds.

23. The neutron source of claim 22, wherein the plug further comprises one or more vent holes that permits the gas generated by the neutron emitting source material to escape into a gas compartment, the casing further comprising one or more vent holes through the walls of the casing that permit the gas in the gas compartment to escape from the capsule.

24. The neutron source of claim 23, wherein the casing further comprises one or more relief flats located on the outside walls of the casing to hold the casing while the plug and the guide wire are threaded into the threads of the casing.

25. A method for treating a tumor in a patient, the method comprising:
   inserting a catheter interstitially into the tumor in the patient;
   attaching a neutron emitting source material to a guide wire;
   using the guide wire to position the neutron emitting source material inside a capsule carrier and within the catheter so that the neutron emitting source material is positioned in the tumor to kill the tumor cells by radioactively decaying and releasing neutrons at a rate between about $2.3 \times 10^8$ and $2.3 \times 10^9$ neutrons per second; and
   attaching the guide wire to the capsule carrier to prevent fluids from contacting the neutron emitting source material.

26. The method of claim 25 further comprising coiling a wire around the guide wire and the catheter so the coiled wire acts as a spring increasing the flexibility and strength of the neutron source device and preventing the neutron source device from kinking.

27. The method of claim 26, wherein the wire is a metal wire.

28. The method of claim 25, wherein attaching the guide wire to the capsule carrier comprises welding the guide wire to the capsule carrier.

29. The method of claim 25, wherein attaching a neutron emitting source material to a guide wire comprises:
   forming the neutron emitting source material into a pellet;
   forming a hole at an end of the guide wire;
   placing the pellet-shaped neutron emitting source material into the hole; and
   forming a weld around the neutron emitting source material.

30. The method of claim 29, wherein forming the neutron emitting source material into a pellet comprises:
   preparing the neutron emitting source material by coating a precipitate of californium oxalate with palladium in an aqueous solution;
   drying the coated calcium oxalate;
   pressed into a pellet at 50% of a desired density; and
   sintered at a temperature of about 1300 degrees, pressed to 90% of the desired density.

31. The method of claim 25, wherein the neutron emitting source material is contained in a capsule positioned inside the capsule carrier.

32. The method of claim 31, wherein the capsule is made of a platinum-iridium alloy.

33. The method of claim 31, wherein the capsule has an outside diameter of about 0.5–2 mm and a length of about 3–6 mm.

34. The method of claim 31 further comprising forming a vent hole in the capsule carrier through which gas escapes from the capsule.

35. The method of claim 31, wherein the capsule is a cylindrical container having an outside diameter between about 0.5–2.0 mm and an inner diameter less than about 1.3 mm.

36. The method of claim 25, wherein attaching the guide wire to the capsule carrier comprises threading the guide wire into a screw hole in the capsule carrier.

37. The method of claim 36, wherein the guide wire has a tapered section so that after the guide wire is threaded into the screw hole, there is a gap between the guide wire and the capsule carrier through which gas can escape.

38. The method of claim 25, wherein positioning the neutron emitting source material inside the catheter comprises inserting the capsule carrier inside the catheter rounded-end first, the capsule carrier including s a rounded end so that the capsule carrier does not damage the catheter upon insertion.

39. The method of claim 25 further comprising:
   making a coil assembly that is shaped to surround the guide wire and the capsule carrier; and
   inserting the coil assembly into the catheter before using the guide wire to position the neutron emitting source material inside the catheter.

40. The method of claim 25 further comprising braiding a plurality of wires to form a braided wire, bundling a plurality of braided wires to form a bundle of braided wires, swaging the bundle of braided wires, fusing together ends of the bundle of braided wires, and grounding down the ends that are fused together to create a guide wire having a smooth outer surface.

* * * * *